(12) United States Patent
Dakka et al.

(10) Patent No.: US 9,249,077 B2
(45) Date of Patent: Feb. 2, 2016

(54) DEHYDROGENATION PROCESS

(75) Inventors: Jihad M. Dakka, Whitehouse Station, NJ (US); Lorenzo C. DeCaul, Langhorne, PA (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 56 days.

(21) Appl. No.: 13/698,830

(22) PCT Filed: Apr. 4, 2011

(86) PCT No.: PCT/US2011/031055
§ 371 (c)(1),
(2), (4) Date: Jan. 11, 2013

(87) PCT Pub. No.: WO2011/162850
PCT Pub. Date: Dec. 29, 2011

(65) Prior Publication Data
US 2013/0204048 A1    Aug. 8, 2013

Related U.S. Application Data

(60) Provisional application No. 61/358,711, filed on Jun. 25, 2010.

(30) Foreign Application Priority Data

Aug. 5, 2010    (EP) ..................... 10171955

(51) Int. Cl.
| | | |
|---|---|---|
| C07C 37/07 | (2006.01) |
| B01J 23/42 | (2006.01) |
| B01J 35/10 | (2006.01) |
| B01J 37/00 | (2006.01) |
| B01J 37/02 | (2006.01) |

(52) U.S. Cl.
CPC ............. C07C 37/07 (2013.01); B01J 23/42 (2013.01); B01J 35/1019 (2013.01); B01J 35/1061 (2013.01); B01J 37/0009 (2013.01); B01J 37/0201 (2013.01)

(58) Field of Classification Search
CPC ....... C07C 37/07; B01J 23/42; B01J 35/1019; B01J 35/1061; B01J 37/0009; B01J 37/0201
USPC .......................................................... 568/799
See application file for complete search history.

(56) References Cited

U.S. PATENT DOCUMENTS

| | | |
|---|---|---|
| 2,291,585 A | 7/1942 | Bartlett et al. |
| 2,321,551 A * | 6/1943 | Loder .......................... 568/799 |
| 3,076,810 A | 2/1963 | Duggan et al. |
| 3,194,843 A | 7/1965 | Silber et al. |
| 3,211,668 A | 10/1965 | Yamamoto |
| 3,238,120 A | 3/1966 | Sale |
| 3,247,278 A | 4/1966 | Garwood et al. |
| 3,358,044 A | 12/1967 | Russell et al. |
| 3,442,958 A | 5/1969 | Choo |
| 3,514,492 A | 5/1970 | Juguin et al. |
| 3,519,575 A | 7/1970 | Bozik et al. |
| 3,534,110 A | 10/1970 | Juguin et al. |
| 3,534,116 A | 10/1970 | Fuller |
| 3,580,970 A | 5/1971 | Swift |
| 3,691,102 A | 9/1972 | Swift |
| 3,775,487 A | 11/1973 | Isbitsky, Jr. et al. |
| 3,933,924 A * | 1/1976 | Weissel et al. ................ 568/747 |
| 4,010,206 A * | 3/1977 | Mikami et al. ................ 568/357 |
| 4,088,603 A | 5/1978 | Carter et al. |
| 4,162,267 A | 7/1979 | Fisher et al. |
| 4,167,456 A | 9/1979 | Murtha |
| 4,169,857 A | 10/1979 | Murtha |
| 4,258,268 A | 3/1981 | Bjornson |

(Continued)

FOREIGN PATENT DOCUMENTS

| | | | |
|---|---|---|---|
| DE | 100 18 724 | 10/2001 | |
| EP | 0316142 | * 11/1988 | .............. C07C 37/07 |
| EP | 1 050 339 | 11/2000 | |
| EP | 1 288 188 | 3/2003 | |
| FR | 1 509 921 | 1/1968 | |
| FR | 1 541 720 | 10/1968 | |
| GB | 986931 | 3/1965 | |
| GB | 1013715 | 12/1965 | |
| JP | 06-263668 | 9/1994 | |
| JP | 07-188082 | 7/1995 | |

(Continued)

OTHER PUBLICATIONS

Arends et al., "*Selective Catalytic Oxidation of Cyclohexylbenzene to Cyclohexylbenzene-1-Hydroperoxide: A Coproduct-Free Route to Phenol*," Tetrahedron, vol. 58, No. 44, pp. 9055-9061 Oct. 28, 2002, ISSN 0040-4020.

(Continued)

*Primary Examiner* — Paul A Zucker
*Assistant Examiner* — Mark Luderer
(74) *Attorney, Agent, or Firm* — Stephen Baehl; Siwen Chen (57) ABSTRACT

In a process for the dehydrogenation of at least one dehydrogenatable hydrocarbon, at least one dehydrogenatable hydrocarbon selected from an oxygen-containing six-membered carbon ring compound is supplied to a first dehydrogenation reaction zone together with at least one stabilizing compound selected from a non-oxygen-containing six membered carbon ring compound to the first dehydrogenation reaction zone, such that the weight ratio of the stabilizing compound to the dehydrogenatable hydrocarbon supplied to the first dehydrogenation reaction zone is in the range of from 1:200 to 200:1. The dehydrogenation feed stream and the at least one stabilizing compound are contacted with a first dehydrogenation catalyst in the first dehydrogenation reaction zone under dehydrogenation conditions to convert at least a portion of the dehydrogenatable hydrocarbon into an unsaturated six-membered carbon ring compound and hydrogen.

15 Claims, 2 Drawing Sheets

(56) References Cited

U.S. PATENT DOCUMENTS

| | | | |
|---|---|---|---|
| 4,328,372 A | 5/1982 | Wu | |
| 4,417,076 A | 11/1983 | Rozovsky et al. | |
| 4,434,299 A | 2/1984 | Chang et al. | |
| 4,520,129 A | 5/1985 | Murtha | |
| 4,929,762 A * | 5/1990 | Matsunaga et al. | 568/361 |
| 4,933,507 A | 6/1990 | Inoki et al. | |
| 4,999,326 A | 3/1991 | Sikkenga et al. | |
| 5,057,296 A | 10/1991 | Beck | |
| 5,087,792 A | 2/1992 | Cottrell et al. | |
| 5,102,643 A | 4/1992 | Kresge et al. | |
| 5,180,871 A | 1/1993 | Matsunaga et al. | |
| 5,256,348 A | 10/1993 | Waller | |
| 5,292,960 A | 3/1994 | Meier et al. | |
| 5,310,713 A | 5/1994 | Kojima et al. | |
| 5,319,148 A | 6/1994 | Karcher et al. | |
| 5,395,976 A | 3/1995 | Scharschmidt et al. | |
| 5,569,635 A | 10/1996 | Moy et al. | |
| 6,037,513 A | 3/2000 | Chang et al. | |
| 6,376,422 B1 | 4/2002 | McNabb et al. | |
| 6,417,135 B1 | 7/2002 | Dyroff | |
| 6,579,821 B1 | 6/2003 | Ginosar et al. | |
| 6,916,756 B2 | 7/2005 | Schindler et al. | |
| 7,115,538 B2 | 10/2006 | Buchanan et al. | |
| 7,256,149 B2 | 8/2007 | Grey et al. | |
| 7,285,512 B2 | 10/2007 | Bai et al. | |
| 7,285,685 B2 | 10/2007 | Walsdorff et al. | |
| 7,396,798 B2 | 7/2008 | Ma et al. | |
| 7,538,066 B2 | 5/2009 | Soled et al. | |
| 2003/0083527 A1 | 5/2003 | Kuhnle et al. | |
| 2004/0110630 A1 | 6/2004 | Schmidt et al. | |
| 2007/0032681 A1 | 2/2007 | Walsdorff et al. | |
| 2008/0039315 A1 | 2/2008 | Ma et al. | |
| 2009/0215612 A1 | 8/2009 | McCarthy et al. | |
| 2010/0075842 A1 | 3/2010 | Han et al. | |
| 2011/0037022 A1 | 2/2011 | Dakka et al. | |
| 2011/0105805 A1 | 5/2011 | Buchanan et al. | |
| 2012/0302798 A1 | 11/2012 | Dakka et al. | |
| 2012/0316365 A1 | 12/2012 | Xu et al. | |
| 2013/0090499 A1 | 4/2013 | Xu et al. | |

FOREIGN PATENT DOCUMENTS

| | | | |
|---|---|---|---|
| JP | 2637812 | 8/1997 | |
| JP | 2007-269522 | 10/2007 | |
| WO | 00/67902 | 11/2000 | |
| WO | 2007/009904 | 1/2007 | |
| WO | 2008/128638 | 10/2008 | |
| WO | WO2009/131769 | * 10/2009 | C07C 37/08 |
| WO | 2009/134514 | 11/2009 | |
| WO | 2010/024975 | 3/2010 | |
| WO | WO 2010/024975 | 3/2010 | |

OTHER PUBLICATIONS

U.S. Appl. No. 13/698,830, filed Jan. 11, 2013.
Borade et al., "Selective Dehydrogenation of Cyclohexene to Benzene using Pd-Exchanged a-Zirconium Phosphate", Catalysis Letters, 1997, vol. 45, pp. 233-235.
Cesar et al., "Stability and Selectivity of Bimetallic Cu-Co/SiO2 Catalysts for Cyclohexanol Dehydrogenation", Applied Catalysis A: General, 1999, vol. 176, No. 2, pp. 205-212.
Chen et al., "Nonoxidative Dehydrogenation of Cyclohexanol over Copper-Iron Binary Oxides", Applied Catalysis A: General, 1992, vol. 83, No. 2, pp. 201-211.
Corma, "From Microporous to Mesoporous Molecular Sieve Materials and Their Use in Catalysis", Chem. Rev., 1997, vol. 97, pp. 2373-2419.
Dobrovolszky et al., "Catalytic Transformations of Cyclohexanol on Group VIII Metal Catalysts", Journal of Catalysis, 1982, vol. 74, No. 1, pp. 31-43.
Fridman et al., "Dehydrogenation of Cyclohexanol on Copper-Containing Catalysts. The Influence of the Oxidation State of Copper on the Activity of Copper Sites", Journal of Catalysis, 2000, vol. 111, No. 1, pp. 20-30.
Fridman et al., "Dehydrogenation of Cyclohexanol Over Copper-Zinc Catalysts", Neftekhimiya, 1989, vol. 29, No. 1, pp. 48-51—English Abstract Only.
Kamiguchi et al., "Catalytic Hydrodehydration of Cyclohexanone, Hydrogenation of 2-Cyclohexen-1-one, and Dehydrogenation of Cyclohexene over a Mo Chloride Cluster with an Octahedral Metal Framework", Journal of Cluster Science, 2005, vol. 16, No. 1, pp. 77-91.
Lezanska et al., "Characterization of Cr-MCM-41 and Al, Cr-MCM-14 Mesoporous Catalyst for Gas-Phase Oxidative Dehydrogenation of Cyclohexane", J. Phys. Chem. C., 2007, vol. 111, pp. 1830-1839.
Masai et al., "Dehydrogenation and Hydrogenation Activity of Palladium-Tin-Silica and Nickel-Tin-Silica", Journal of Catalysis, 1977, vol. 50, No. 3, pp. 419-428.
Masai et al., "Dehydrogenation Activity of Nickel-Tin-Silica Catalyst", Journal of Catalysis, 1975, vol. 38, pp. 128-134.
Milczanowski et al., "Catalytic Dehydrogenation of Cyclohexanone to Phenol", PrZEMYSL Cheniczny, 1978, vol. 57, No. 3, pp. 129-130—English Abstract Only.
Nikiforova et al., "Dehydrogenation of Cyclohexanol over Copper Supported on Magnesia", Neftekhimiya, 1973, vol. 78, No. 4, pp. 475-480.
Paal et al., "A Radiotracer Investigation of Transformations of Cyclohexanol in the Presence of a Nickel Powder Catalyst", Z Phys Chem, 1974, vol. 91, No. 1-4, pp. 54-66.
Saito et al. "Performance of activity test on supported Pd catalysts for dehydrogenation of cyclohexanone to phenol (effect of supports on activity)", Ibaraki Kogyo Koto Senmon Gakko Kenkyu Iho, 1995, vol. 30, pp. 39-46—English Abstract Only.
Samolada et al., "Catalyst Evaluation for Catalytic Biomass Pyrolysis", Energy & Fuels, 2000, vol. 14, pp. 1161-1167.
Solsona et al., "Vanadium Oxide Supported on Mesoporous MCM-41 as Selective Catalyst in the Oxidative Dehydrogenation of Alkanes", Journal of Catalysis, 2001, vol. 203, pp. 443-452.
Spieker et al., "Experimental Investigation and Modeling of Platinum Adsorption onto Ion-moded Silica and Alumina", Studies in Surface Science and Catalysis, 2000, vol. 130, pp. 203-208.
Swift et al., "Metallic Phases and Activites of Nickel-Tin-Silica Catalysts Dehydrogenation of Cyclohexanone, Cyclohexanol, and Cyclohexane", Journal of Catalysis, 1968, vol. 12, pp. 5-14.
Waligora et al., "Catalytic Dehydrogenation of Mixture of Cyclohexanol and Cyclohexanon to Phenol", Prace Chemiczne, 1982, vol. 27, pp. 93-99—English Abstract Only.

* cited by examiner

DEHYDROGENATION PROCESS

PRIORITY CLAIM TO RELATED APPLICATIONS

This application is a National Stage Application of International Application No. PCT/US2011/031055 filed Apr. 4, 2011, which claims priority to U.S. Provisional Application Ser. No. 61/358,711 filed Jun. 25, 2010, and European Application No. 10171955.7, filed Aug. 5, 2010, the disclosures of which are fully incorporated herein by their reference.

CROSS REFERENCE TO RELATED APPLICATIONS

This application is related to U.S. application Ser. No. 12/996,219 filed Jul. 14, 2009, (2008EM224); International Patent Cooperation Treaty Application Nos. PCT/US2010/061037, filed Feb. 8, 2007 (2010EM042); PCT/US2010/061012, filed Dec. 17, 2010 (2010EM022); and PCT/US2010/061050, filed Dec. 17, 2010 (2010EM044).

FIELD

The present invention relates to a process for dehydrogenating a dehydrogenatable hydrocarbon selected from an oxygen-containing six-membered carbon ring compound.

BACKGROUND

Various dehydrogenation processes have been proposed to dehydrogenate dehydrogenatable hydrocarbons such as cyclohexanone and cyclohexane. For example, these dehydrogenation processes have been used to convert at least a portion of cyclohexanone into phenol.

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone.

Other known routes for the production of phenol involve the direct oxidation of benzene, the oxidation of toluene, and the oxidation of s-butylbenzene wherein methyl ethyl ketone is co-produced with phenol in lieu of acetone produced in the Hock process.

Additionally, phenol can be produced by the oxidation of cyclohexylbenzene to cyclohexylbenzene hydroperoxide wherein cyclohexanone is co-produced with phenol in lieu of acetone produced in the Hock process. A producer using this process may desire to dehydrogenate at least a portion of the cyclohexanone produced into the additional phenol depending on market conditions.

Thus in International Patent Application WO 2010/024975 filed Jul. 14, 2009, a process has been proposed for producing phenol by oxidation of cyclohexylbenzene to cyclohexylbenzene hydroperoxide followed by cleavage of the cyclohexylbenzene hydroperoxide, in which at least a portion of the effluent from the cleavage step is subjected to a dehydrogenation step. The dehydrogenation not only converts at least a portion of the cyclohexanone in the effluent portion to additional phenol but also generates hydrogen as a by-product, which can, for example, be recycled to an initial benzene hydroalkylation step for producing the cyclohexylbenzene feed. In addition, although the cleavage effluent portion subjected to the dehydrogenation step can be a substantially pure cyclohexanone fraction produced by separation of the phenol and light and heavy ends from the raw effluent, given the cost of this separation, the process can also be applied to an effluent portion containing some or all of the phenol produced in the cleavage step. In this way, the total cost of purifying the final phenol stream and the amount, if any, of the final cyclohexanone stream can be minimized.

Currently, however, the viability of this method of controlling the cyclohexanone content in the product of the Hock process via cyclohexylbenzene is the stability of the dehydrogenation catalyst, since most existing catalysts capable of promoting the dehydrogenation of cyclohexanone to phenol deactivate rapidly and hence require frequent reactivation and/or replacement. Surprisingly, it has now been found that a significant improvement in catalyst stability in the dehydrogenation of cyclohexanone can be achieved by co-feeding at least one of cyclohexane, cyclohexene and benzene with the cyclohexanone. This is an important discovery, particularly in the case of cyclohexane, since cyclohexane is a major and currently unwanted by-product of the initial benzene hydroalkylation process. Under the conditions of the cyclohexanone dehydrogenation step, the cyclohexane is converted via cyclohexene to benzene, which can be recycled to the benzene hydroalkylation step. Thus the present method not only improves the cyclohexanone dehydrogenation step but also addresses a significant problem of the benzene hydroalkylation step.

SUMMARY

In one aspect, the invention resides in a process for the dehydrogenation of at least one dehydrogenatable hydrocarbon, the process comprising:

(a) supplying a dehydrogenation feed stream comprising at least one dehydrogenatable hydrocarbon to a first dehydrogenation reaction zone wherein the at least one dehydrogenatable hydrocarbon is an oxygen-containing six-membered carbon ring compound;

(b) supplying at least one stabilizing compound to the first dehydrogenation reaction zone, such that the weight ratio of the stabilizing compound to the dehydrogenatable hydrocarbon supplied to the first dehydrogenation reaction zone is in the range of from 1:200 to 200:1 wherein the stabilizing compound is a non-oxygen-containing six membered carbon ring compound; and (c) contacting the at least one dehydrogenatable hydrocarbon and the at least one stabilizing compound with a first dehydrogenation catalyst in the first dehydrogenation reaction zone under dehydrogenation conditions to convert at least a portion of the dehydrogenatable hydrocarbon into an unsaturated six-membered carbon ring compound and hydrogen.

Conveniently, the at least one stabilizing compound is selected from cyclohexane, cyclohexene, and benzene.

Conveniently, the at least one dehydrogenatable hydrocarbon is cyclohexanone and the unsaturated six-membered carbon ring compound is phenol.

Conveniently, the weight ratio of the stabilizing compound to the cyclohexanone supplied to the first dehydrogenation reaction zone is at least 1:200 to 200:1.

In one embodiment, the dehydrogenation feed stream is produced by a process comprising:

(d) contacting benzene and hydrogen with a hydroalkylation catalyst under hydroalkylation conditions to produce a hydroalkylation reaction product stream comprising cyclohexylbenzene, cyclohexane, and benzene;

(e) oxidizing at least a portion of the cyclohexylbenzene from the hydroalkylation reaction product stream to produce cyclohexylbenzene hydroperoxide;

(f) cleaving at least a portion of the cyclohexylbenzene hydroperoxide from the oxidizing;

(e) to produce a cleavage reaction product stream comprising phenol and cyclohexanone; and (g) employing at least a portion of the cleavage reaction product stream as the first dehydrogenation feed stream.

Conveniently, the at least one stabilizing compound is obtained from the hydroalkylation reaction product stream.

In one embodiment, at least a portion of the hydroalkylation reaction product stream is divided into (i) a $C_6$-rich stream comprising cyclohexane and benzene; and (ii) a cyclohexylbenzene-rich stream.

Conveniently, at least a portion of the $C_6$-rich stream is supplied to the first dehydrogenation reaction zone as the at least one stabilizing compound. Generally, at least a portion of the cyclohexane in the portion of the $C_6$-rich stream is converted to benzene by the contacting (c) and at least a portion of the benzene is recycled to the contacting (d).

Conveniently, a further portion of the $C_6$-rich stream is supplied to a second dehydrogenation reaction zone and contacting the further portion of the $C_6$-rich stream with a second dehydrogenation catalyst in the second dehydrogenation reaction zone under dehydrogenation conditions to convert at least a portion of the cyclohexane into benzene and produce a second dehydrogenation product stream. Typically, at least a portion of the second dehydrogenation product stream is recycled back to the contacting (d).

In one embodiment, at least a portion of the cleavage reaction product stream is supplied without fractionation to the first dehydrogenation reaction zone as the dehydrogenation feed stream.

In another embodiment, the method further comprises distilling at least a portion of the cleavage reaction product stream into (i) a first fraction comprising an azeotropic mixture of phenol and cyclohexanone; and (ii) a second fraction rich in cyclohexanone. Conveniently, at least a portion of the first fraction is supplied to the first dehydrogenation reaction zone as the dehydrogenation feed stream. Alternatively, at least a portion of the second fraction is supplied to the first dehydrogenation reaction zone as the dehydrogenation feed stream.

DESCRIPTION OF THE EMBODIMENTS

Described herein is a process for dehydrogenating a dehydrogenatable hydrocarbon in which a feed stream comprising a dehydrogenatable hydrocarbon selected from an oxygen-containing six-membered carbon ring compound is supplied to a first dehydrogenation reaction zone together with at least one stabilizing compound selected from a non-oxygen-containing six membered carbon ring compound. The dehydrogenatable hydrocarbon-containing feed stream and the at least one stabilizing compound are then contacted with a first dehydrogenation catalyst in the first dehydrogenation reaction zone under dehydrogenation conditions sufficient to convert at least a portion of the dehydrogenatable hydrocarbon into an unsaturated six-membered carbon ring compound and hydrogen to produce a first dehydrogenation product stream.

In one embodiment, the non-oxygen-containing six membered ring compound is selected from cyclohexane, cyclohexene, and benzene. In another embodiment, the non-oxygen-containing six membered ring compound is selected from cyclohexane and cyclohexene. In still another embodiment, the non-oxygen-containing six membered ring compound is cyclohexane. In other embodiments, the non-oxygen-containing six membered carbon ring compound is selected from alkyl-substituted non-oxygen-containing six membered carbon ring compounds such as methylcyclohexane, methylcyclohexene and methylbenzene.

Typically, the at least one stabilizing compound is supplied to the first dehydrogenation reaction zone in an amount such that the weight ratio of the stabilizing compound(s) to the dehydrogenatable hydrocarbon supplied to the first dehydrogenation reaction zone is at least 1:1000, such as at least 1:200, at least 1:100, at least 1:50, at least 1:25, at least 1:10, at least 1:5. In one embodiment, the weight ratio of the stabilizing compound(s) to the dehydrogenatable hydrocarbon is no greater than 1:1. In another embodiment, the at least one stabilizing compound is supplied to the first dehydrogenation reaction zone in an amount such that the weight ratio of the stabilizing compound(s) to the dehydrogenatable hydrocarbon supplied to the first dehydrogenation reaction zone is in the range of from 1:1000 to 1000:1, 1:200 to 200:1; from 1:100 to 100:1; 1:75 to 75:1; 1:50 to 50:1; from 1:10 to 10:1 and from 1:5 to 5:1.

In one embodiment, the dehydrogenatable hydrocarbon is selected from cyclohexanone, cyclohexenone, cyclohexanol, cyclohexenol, hydroxy cyclohexanones, and cyclohexyldiones or a mixture thereof.

In another embodiment, the dehydrogenatable hydrocarbon is cyclohexanone and the unsaturated six-membered carbon ring compound is phenol.

Although the cyclohexanone-containing feed stream employed in the present process can be prepared by any known method, in one preferred embodiment the cyclohexanone-containing feed stream is produced as an intermediate reaction product of the Hock process for producing phenol via cyclohexylbenzene. In such a process benzene is initially converted to cyclohexylbenzene, the cyclohexylbenzene is then oxidized to cyclohexylbenzene hydroperoxide and the cyclohexylbenzene hydroperoxide is cleaved to produce phenol and cyclohexanone. The following description will focus on this preferred route for producing the cyclohexanone-containing feed stream employed in the present process.

Production of the Cyclohexylbenzene

Any known process can be used to effect the initial conversion of benzene to cyclohexybenzene, including alkylation of the benzene with cyclohexene in the presence of an acid catalyst, such as zeolite beta or an MCM-22 family molecular sieve, or by oxidative coupling of the benzene to biphenyl followed by hydrogenation of the biphenyl. However, in practice, the cyclohexylbenzene is generally produced by contacting the benzene with hydrogen under hydroalkylation conditions in the presence of a hydroalkylation catalyst whereby the benzene undergoes the following reaction (1) to produce cyclohexylbenzene (CHB):

(1)

Any commercially available benzene feed can be used in the hydroalkylation reaction, but preferably the benzene has a purity level of at least 99 wt %. Similarly, although the source of hydrogen is not critical, it is generally desirable that the hydrogen is at least 99 wt % pure.

Conveniently, the total feed to the hydroalkylation reaction contains less than 1000 ppm, such as less than 500 ppm, for example less than 100 ppm, water. In addition, the total feed typically contains less than 100 ppm, such as less than 30 ppm, for example less than 3 ppm, sulfur; less than 10 ppm, such as less than 1 ppm, for example less than 0.1 ppm, nitrogen and less than 100 ppm, such as less than 10 ppm, for example less than 1 ppm, CO.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst employed in the hydroalkylation reaction is preferably a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference).

Molecular sieves of MCM-22 family generally have an X-ray diffraction pattern including d-spacing maxima at −12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Ga. and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation reaction using an MCM-22 family zeolite catalyst is highly selective towards cyclohexylbenzene, the effluent from the hydroalkylation reaction will likely contain significant quantities of unreacted benzene and certain by-products in addition the desired cyclohexylbenzene. Generally, the major by-products are cyclohexane and dicyclohexylbenzene. A multi-stage distillation process is therefore used to divide the hydroalkylation reaction product into (i) a $C_6$-rich stream comprising cyclohexane; (ii) a cyclohexylbenzene-rich stream; and (iii) a heavies stream rich in dicyclohexylbenzene. Owing to the similarity in the boiling points of benzene and cyclohexane, the $C_6$-rich stream is difficult to further separate by simple distillation. However, as will be explained in detail below, an advantage of the present process is that at least a portion of the $C_6$-rich stream can be used directly as a stabilizing compound in the subsequent cyclohexanone dehydrogenation process.

Depending on the amount of dicyclohexylbenzene present in the heavies stream (iii), it may be desirable to either (a)

transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, zeolite USY, and mordenite. The transalkylation reaction is typically conducted under liquid phase conditions, which suitably include a temperature of about 100 to about 300° C., a pressure of about 800 to about 3500 kPa, a weight hourly space velocity of about 1 to about 10 hr$^{-1}$ on total feed, and a benzene/dicyclohexylbenzene weight ratio about of 1:1 to about 5:1.

The cyclohexylbenzene-rich stream (ii) separated from the hydroalkylation reaction product is fed to the oxidation reaction described in more detail below.

Oxidation of the Cyclohexylbenzene

In order to convert the cyclohexylbenzene into phenol and cyclohexanone, the cyclohexylbenzene is initially oxidized to cyclohexylbenzene hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N"-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Cleavage of the Cyclohexylbenzene Hydroperoxide

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase. A suitable heterogeneous catalyst for use in the cleavage of cyclohexylbenzene hydroperoxide includes a smectite clay.

Treatment of Cleavage Effluent

The effluent from the cleavage reaction comprises phenol and cyclohexanone in substantially equimolar amounts, generally together with at least one of cyclohexanol, cyclohexenol, and cyclohexenone. The present process provides an advantageous route to increasing the amount of phenol produced from the original benzene feed by dehydrogenating at least a portion of the cyclohexanone in the cleavage effluent into additional phenol according to the reaction (2):

Depending on the amount of the cyclohexanone in the cleavage effluent to be converted into additional phenol, the cyclohexanone can be partially or completely separated from the cleavage effluent prior to be subjected to the dehydrogenation reaction. It is, however, to be appreciated that a mixture of phenol and cyclohexanone cannot be separated by simple distillation since the latter produces a first fraction comprising an azeotropic mixture of 72 wt % phenol and 28 wt % cyclohexanone and (ii) a second fraction rich in cyclohexanone. Thus, in one practical embodiment, the cleavage effluent is subjected to distillation and the first azeotropic phenol/cyclohexanone fraction is subjected to dehydrogenation to convert at least a portion of the cyclohexanone in the fraction to additional phenol. The second cyclohexanone-rich fraction can then either be recovered or separately dehydrogenated to additional phenol.

The dehydrogenation process comprises contacting the cyclohexanone-containing feed with a dehydrogenation catalyst in a first dehydrogenation zone to produce a first dehydrogenation product stream. In one embodiment, the cyclohexanone-containing feed will also comprise cyclohexanol in amounts of from 0.1 to 10 wt %, from 0.5 wt % to 10 wt %, and from 1 wt % to 10 wt % based on the total weight of the cyclohexanone-containing feed. In other embodiments, the cyclohexanol wt % lower limit may be 0.1 wt %, 0.2 wt %, 0.3 wt %, 0.4 wt %, 0.5 wt %, 1 wt %, 2, wt %, 3 wt %, 4 wt % and 5 wt %; and the cyclohexanol wt % upper limit temperature may be 1 wt %, 3 wt %, 5 wt %, 7 wt %, 10 wt %, 20 wt %, and 50 wt % based on the total weight of the cyclohexanone-containing feed with ranges from any lower limit to any upper limit being contemplated.

The dehydrogenation process generally takes place in a fixed bed reactor, under dehydrogenation conditions typically including a temperature of about 250° C. to about 500° C., a pressure of about 0 psig to about 500 psig (100 kPa to 3550 kPa), a weight hourly space velocity of about 0.2 to 50 $hr^{-1}$, and a hydrogen to cyclohexanone-containing feed molar ratio of about 0 to about 20.

The catalyst employed in the cyclohexanone dehydrogenation reaction generally comprises (i) a support; (ii) a hydrogenation-dehydrogenation component; and (iii) an inorganic promoter. Conveniently, the support (i) is selected from the group consisting of silica, a silicate, an aluminosilicate, zirconia, and carbon nanotubes, and preferably comprises silica. Suitable hydrogenation-dehydrogenation components (ii) comprise at least one metal selected from Groups 6 to 10 of the Periodic Table of Elements and compounds and mixtures thereof, such as platinum, palladium and compounds and mixtures thereof. Typically, the hydrogenation-dehydrogenation component is present in an amount between about 0.1 and about 10 wt % of the catalyst. In addition, the catalyst comprises an inorganic promoter (iii) comprising at least one metal or compound thereof selected from Group 1 of the Periodic Table of Elements, such as a potassium compound. Typically, the promoter is present in an amount between about 0.1 and about 5 wt % of the catalyst.

Preferably, the cyclohexanone dehydrogenation catalyst exhibits an oxygen chemisorption of greater than 0.5, preferably greater than 0.6 and more preferably greater than 0.7. As used herein, the oxygen chemisorption value of a particular catalyst is a measure of metal dispersion on the catalyst and is defined as the ratio of the number of moles of atomic oxygen sorbed by the catalyst to the number of moles of dehydrogenation metal contained by the catalyst. The oxygen chemisorption values referred to herein are measured using the technique described in the Examples with a Micromeritics ASAP 2010 Chemisorption Unit. This is a volumetric device that allows treatment of material using an array of gases. A thermal conductivity cell (TCD) is used for detection of the active species in the effluent stream from the sample cell. The oxygen technique involves an in-situ calcination at low temperature followed by activation of the metals using gas-phase sulfiding with 10% $H_2S/H_2$ gas. After the metals are sulfided, they are "titrated" by exposure to sequential, fixed-volume pulses of 10% $O_2$/helium until oxidation is complete and $O_2$ breakthrough is achieved.

When fresh, the dehydrogenation catalyst described herein is highly active and selective for the conversion of cyclohexanone to phenol. However, without the provision of some means for stabilizing the catalyst, it is found that the catalyst rapidly loses activity so that the amount of conversion of the cyclohexanone rapidly decreases with time on stream. Thus, in the present dehydrogenation process, at least one stabilizing compound, selected from cyclohexane, cyclohexene and benzene, is supplied to the first dehydrogenation reaction zone in addition to the cyclohexanone. In another embodiment the at least one stabilizing compound is selected from cyclohexane and cyclohexene. Typically, the at least one stabilizing compound is supplied to the first dehydrogenation reaction zone in an amount such that the weight ratio of the stabilizing compound(s) to the cyclohexanone supplied to the first dehydrogenation reaction zone is in the range of from 1:1000 to 1000:1, 1:200 to 200:1; from 1:100 to 100:1; 1:75 to 75:1; 1:50 to 50:1; from 1:10 to 10:1 and from 1:5 to 5:1. In another embodiment, the weight ratio of the stabilizing compound(s) to the cyclohexanone supplied to the first dehydrogenation reaction zone is at least 1:1000, such as at least 1:200, at least 1:100, at least 1:50, at least 1:25, at least 1:10, at least 1:5, and no greater than 1:1. Surprisingly, the stabilizing compound significantly reduces the loss of activity of the dehydrogenation catalysts with time on stream without reducing the selectivity of the conversion of the cyclohexanone to phenol. Moreover, where the stabilizing compound is cyclohexane and/or cyclohexene, the conditions in the first dehydrogenation reaction zone are sufficient not only to convert the cyclohexanone to phenol but also to convert the cyclohexane via cyclohexene to benzene. Since cyclohexane is a major by-product of the initial benzene hydroalkylation process and cannot readily be separated from the unreacted benzene in the hydroalkylation product, the $C_6$-rich stream (composed mainly of cyclohexane and unreacted benzene) resulting from distillation of the hydroalkylation product is a particularly useful source of the at least one stabilizing compound. The benzene-enriched $C_6$ stream produced by dehydrogenation process can be removed from the dehydrogenation reaction product and recycled to the hydroalkylation reaction.

In some cases, only a portion of the $C_6$-rich stream separated from the hydroalkylation product is fed as a stabilizing compound to the first dehydrogenation reaction zone. In such cases, a further portion of the $C_6$-rich stream may be supplied to a second dehydrogenation reaction zone and contacted with a second dehydrogenation catalyst under dehydrogenation conditions sufficient to convert at least a portion of the cyclohexane in the further $C_6$-rich stream portion to benzene, which again can be recycled to the hydroalkylation reaction.

The first dehydrogenation reaction zone and the second dehydrogenation reaction zone may each comprise of one or multiple reactors. Where more than one reactors are involved, the reactors may be placed either in series or parallel.

Figure 1:
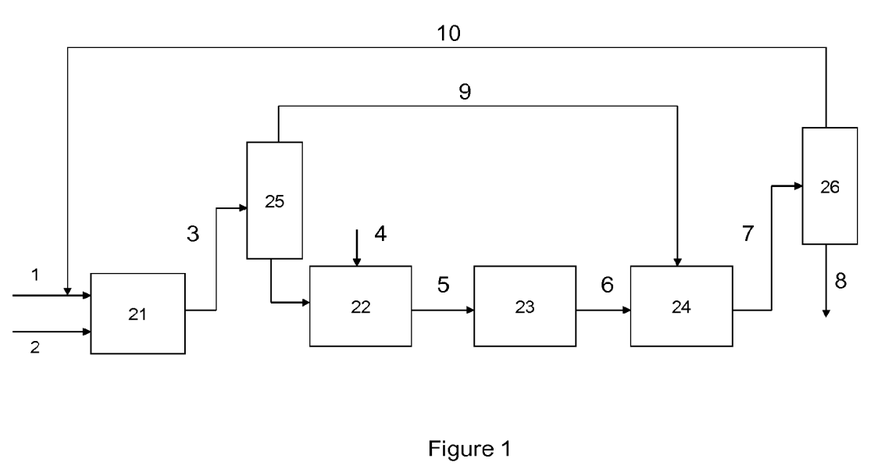
FIG. 1 is a flow diagram of an integrated process according to one example of the invention for converting benzene to phenol via benzene hydroalkylation and for dehydrogenating the co-produced cyclohexanone.

One embodiment of the present process is shown in FIG. 1, in which benzene and hydrogen are supplied by lines 1 and 2, respectively, to a hydroalkylation reactor 21. The hydroalkylation reaction product is fed by line 3 from reactor 21 to a first distillation column 25, where the hydroalkylation reaction product is divided into an overhead $C_6$-rich stream comprising cyclohexane and unreacted benzene in line 9 and a bottoms stream comprising cyclohexylbenzene. The bottoms stream is fed to an oxidation reactor 22, which also receives air via line 4. The cyclohexylbenzene is oxidized in the reactor 22 to cyclohexylbenzene hydroperoxide which is fed via line 5 to a cleavage reactor 23. The cyclohexylbenzene hydroperoxide is converted in the cleavage reactor 23 to a cleavage product stream which comprises phenol and cyclohexanone and which is supplied via line 6 to a dehydrogenation reactor 24. The dehydrogenation reactor 24 also receives at least a portion of the $C_6$-rich stream from line 9 and is operated under conditions to convert the cyclohexanone in the cleavage product stream to phenol and the cyclohexane in the $C_6$-rich stream to benzene. The product of the dehydrogenation reaction is removed from the reactor 24 via line 7 and fed to a second distillation column 26 where the dehydrogenation reaction product is separated into a phenol-rich stream, which is recovered for purification in line 8, and a benzene-rich stream which is recycled to the hydroalkylation reactor 21 via line 10.

Provided are one or more embodiments:

A. A process for the dehydrogenation of at least one dehydrogenatable hydrocarbon, the process comprising:
   a) supplying a dehydrogenation feed stream comprising at least one dehydrogenatable hydrocarbon to a first dehydrogenation reaction zone wherein the at least one dehydrogenatable hydrocarbon is an oxygen-containing six-membered carbon ring compound;
   b) supplying at least one stabilizing compound to the first dehydrogenation reaction zone, such that the weight ratio of the stabilizing compound to the dehydrogenatable hydrocarbon supplied to the first dehydrogenation reaction zone is in the range of from 1:200 to 200:1 wherein the stabilizing compound is a non-oxygen-containing six membered carbon ring compound; and
   c) contacting the at least one dehydrogenatable hydrocarbon and the at least one stabilizing compound with a first dehydrogenation catalyst in the first dehydrogenation reaction zone under dehydrogenation conditions to convert at least a portion of the dehydrogenatable hydrocarbon into an unsaturated six-membered carbon ring compound and hydrogen.

B. The process of embodiment A, wherein the weight ratio of the stabilizing compound to the dehydrogenatable hydrocarbon supplied to the first dehydrogenation reaction zone is in the range of from 1:100 to 10:1.

C. The process of any preceding embodiment, wherein the weight ratio of the stabilizing compound to the dehydrogenatable hydrocarbon supplied to the first dehydrogenation reaction zone in the range of from 1:200 to 1:1.

D. The process of any preceding embodiment, wherein the at least one stabilizing compound is selected from cyclohexane, cyclohexene and benzene.

E. The process of any preceding embodiment, wherein the at least on stabilizing compound is cyclohexane.

F. The process of any preceding embodiment, wherein the at least one stabilizing compound is benzene.

G. The process of any preceding embodiment, wherein the at least one dehydrogenatable hydrocarbon is cyclohexanone and the unsaturated six-membered carbon ring compound is phenol.

H. The process of embodiment G, wherein the dehydrogenation feed stream is produced by a process comprising:
   (d) contacting benzene and hydrogen with a hydroalkylation catalyst under hydroalkylation conditions to produce a hydroalkylation reaction product stream comprising cyclohexylbenzene, cyclohexane, and benzene;
   (e) oxidizing at least a portion of the cyclohexylbenzene from the hydroalkylation reaction product stream to produce cyclohexylbenzene hydroperoxide;
   (f) cleaving at least a portion of the cyclohexylbenzene hydroperoxide from the oxidizing step (e) to produce a cleavage reaction product stream comprising phenol and cyclohexanone; and
   (g) employing at least a portion of the cleavage reaction product stream as the dehydrogenation feed stream.

I. The process of embodiment H, wherein the at least one stabilizing compound is obtained from the hydroalkylation reaction product stream.

J. The process of any one of embodiments H and I, and further comprising dividing at least a portion of the hydroalkylation reaction product stream into (i) a $C_6$-rich stream comprising cyclohexane and benzene; and (ii) a cyclohexylbenzene-rich stream.

K. The process of embodiment J, and further comprising supplying at least a portion of the $C_6$-rich stream to the first dehydrogenation reaction zone as the at least one stabilizing compound.

L. The process of any one of embodiments J and K, wherein at least a portion of the cyclohexane in the $C_6$-rich stream is converted to benzene by the contacting step (c) and at least a portion of the benzene is recycled to the contacting step (d).

M. The process of any one of embodiments J and L, and further comprising supplying a further portion of the $C_6$-rich stream to a second dehydrogenation reaction zone and contacting the further portion of the $C_6$-rich stream with a second dehydrogenation catalyst in the second dehydrogenation reaction zone under dehydrogenation conditions to convert at least a portion of the cyclohexane into benzene and produce a second dehydrogenation product stream.

N. The process of any one of embodiments J and M, and further comprising recycling at least a portion of the second dehydrogenation product stream back to the contacting step (d).

O. The process of any one of embodiments H to N, wherein at least a portion of the cleavage reaction product stream is supplied without fractionation to the first dehydrogenation reaction zone as the dehydrogenation feed stream.

P. The process of any one of embodiments H to O, and further comprising distilling at least a portion of the cleavage reaction product stream into (i) a first fraction comprising an azeotropic mixture of phenol and cyclohexanone; and (ii) a second fraction rich in cyclohexanone.

Q. The process of embodiment P, wherein at least a portion of the first fraction is supplied to the first dehydrogenation reaction zone as the dehydrogenation feed stream.

R. The process of any one of embodiments P to Q, wherein at least a portion of the second fraction is supplied to the first dehydrogenation reaction zone as the dehydrogenation feed stream.

S. The process of any one of embodiments H to R, wherein the hydroalkylation reaction product stream further comprises dicyclohexylbenzene and the dicyclohexylbenzene is converted to additional cyclohexylbenzene either by dealkylation or by transalkylation with benzene.

The invention will now be more particularly described with reference to the following non-limiting Examples and the accompanying drawings.

Example 1

Catalyst Preparation (0.8 wt % Pt/1 wt % L/SiO$_2$)

0.403 gram of hexachloroplatonic acid was dissolved in 25 cc of a 4:1 wt ratio acetone/water mixture. This solution was added to 20 grams of SiO$_2$ extrudate having a surface area of 130 m$^2$/gram and a pore diameter of 300-400 Angstrom. The mixture was left overnight at room temperature to evaporate excess water. The metal impregnated catalyst was then dried at 100° C. Then 25 grams of a potassium carbonate solution (0.71 gram potassium carbonate in an acetone/water 4:1 wt ratio mixture) was added to the Pt/SiO$_2$ extrudate sample. The mixture was left overnight at room temperature to evaporate water and was then dried at 100° C.

Example 2

Cyclohexanone Dehydrogenation

The reactor used in this experiment consisted of a stainless steel tube with dimensions of 22 inch (56 cm) in length, ½ inch (1.3 cm) external diameter and 0.035 inch (0.09 cm) wall thickness. A piece of stainless steel tubing 8.75 inch (22 cm) in length and 0.375 inch (1 cm) external diameter surrounding a piece of 0.25 inch (0.6 cm) external diameter tubing of similar length was used in the bottom of the reactor as a spacer to position and support the catalyst in the isothermal zone of a furnace. A 0.25 inch (0.6 cm) plug of glass wool was placed at the top of the spacer to keep the catalyst in place. A 0.125 inch (0.3 cm) stainless steel thermo-well was placed in the catalyst bed, long enough to monitor temperature throughout the catalyst bed using a movable thermocouple.

The catalyst produced in Example 1 was pressed into pellets and then crushed and sized to 20 to 40 US sieve mesh. Typically 5.0 grams (volume 12.5 cc) of the catalyst was pre-sized to 20 to 40 mesh and used as a standard loading. The catalyst was then loaded into the reactor from the top. The catalyst bed typically was 15 cm in length. A 0.25 inch (0.6 cm) plug of glass wool was placed at the top of the catalyst bed to separate the catalyst from quartz chips filling the remaining void space at the top of the reactor. The reactor was installed in the furnace with the catalyst bed in the middle of the furnace at the premarked isothermal zone. The reactor was then pressure and leak tested typically at 300 psig (2170 kPa).

The catalyst was pre-conditioned in situ by heating to 375° C. to 430° C. with $H_2$ flow at 100 cc/min and holding for 2 hrs. After pre-conditioning, a 500 cc ISCO syringe pump was used to introduce a mixture of cyclohexanone/cyclohexanol/cyclohexane to the reactor. The feed was pumped through a vaporizer before flowing through heated lines to the reactor. A Brooks mass flow controller was used to set the hydrogen flow rate. A Grove 'Mity Mite" back pressure controller was used to control the reactor pressure, typically at 100 psig (790 kPa). GC analyses were taken to verify feed composition. The feed was then pumped through the catalyst bed held at the reaction temperature of 375° C. to 430° C., preferably at 430° C., at a LHSV of 2 and a pressure of 100 psig (790 kPa). The products exiting the reactor flowed through heated lines routed to two collection pots in series, the first pot being heated to 60° C. and the second pot cooled with chilled coolant to about 10° C. The non-condensable gas products were routed to an on line Hewlett Packard 5890 gas chromatograph.

The products were collected for material balances over 12 hrs to 24 hrs intervals. Samples were taken and diluted with 50% ethanol for analysis. A Hewlett Packard 6890 gas chromatograph with FID detector and with an Agilent technologies GC column 30 m×0.32 mm×0.25 micron film thickness was used for the analyses of the condensable hydrocarbon products. Non-condensable gas products analyses were taken on line via the HP 5980 Gas Chromatograph with J and W Scientific column 60 m×0.25 mm ID×1.0 micron film. The HP 6890GC analysis ramp program was set to: 40° C. for 0 min; 5° C./min to 150° C., held 0 min; 10° C./min to 260° C. held 28 min, with the total analysis time being 60 min. The HP 5890 GC ramp was set to: −30° C. for 5 min, 5° C./min to 80° C. for 2 min, 5° C./min to 200° C. for 0 min, 15° C./min to 240° C. held to the end total analysis time of 60 min.

Figure 2:
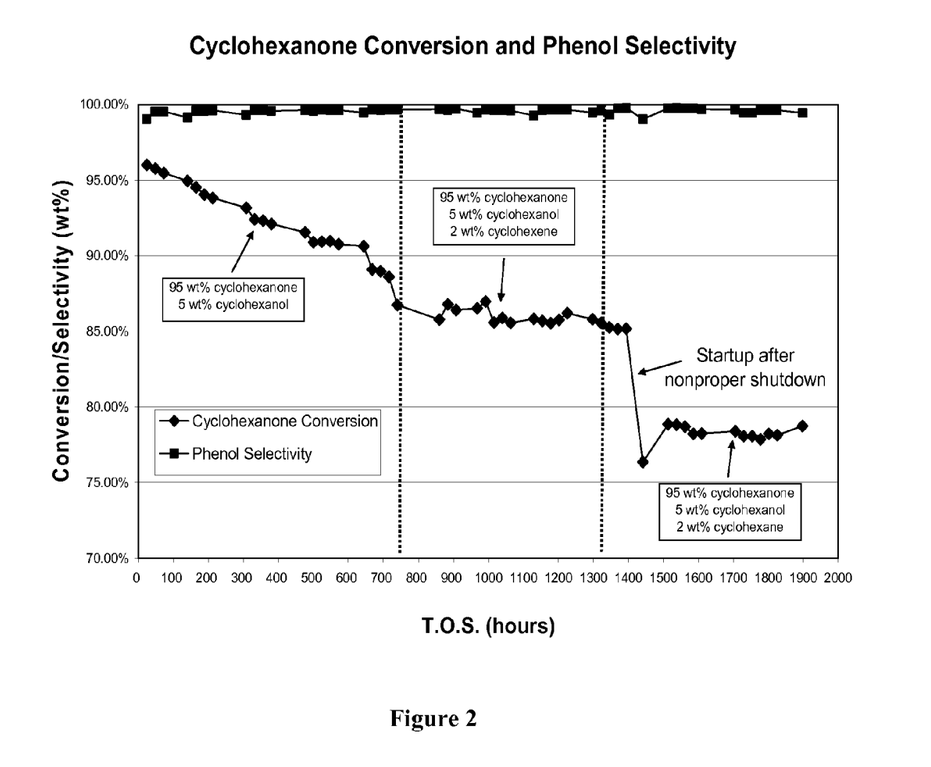
FIG. 2 is a graph of cyclohexanone conversion and phenol selectivity against time on stream for the process of Example 2, 3, and 4 during dehydrogenation of (a) a mixture of 95 wt % cyclohexanone and 5 wt % cyclohexanol from 0 to 740 hours on stream [Example 2]; (b) a mixture of 93 wt % cyclohexanone, 5 wt % cyclohexanol and 2 wt % of cyclohexene from 740 to 1320 hours on stream [Example 3]; and (c) a mixture of 93 wt % cyclohexanone, 5 wt % cyclohexanol and 2 wt % of cyclohexane from 1320 to 1920 hours on stream [Example 4].

A typical time-on-stream (TOS) profile for the above process is shown in FIG. 2. For Example 2, cyclohexanone was dehydrogenated in the presence of 5 wt % cyclohexanol at 2 WHSV yielding a dehydrogenation feed composition of 95 wt % cyclohexanone and 5 wt % cyclohexanol. The data shows that the cyclohexanone conversion dropped from 96% to 86% within 740 hours on stream as represented in FIG. 2.

Example 3

Cyclohexanone Dehydrogenation with Cyclohexene

The test was run at the same conditions as Example 2 with the addition of cyclohexene yielding a feed composition comprising 93 wt % cyclohexanone, 5 wt % cyclohexanol, and 2 wt % cyclohexene. This feed composition was feed to the dehydrogenation reactor for 580 hrs (i.e., from 740 hours to 1320 hours TOS) as represented in FIG. 2. The data show that the cyclohexanone conversion remained the same (86% during the test) during the 580 hour run indicating a dramatic improvement in the catalyst stability. Under these conditions, the cyclohexene is converted to benzene.

Example 4

Cyclohexanone Dehydrogenation with Cyclohexene

The test was run at the same conditions as Example 2 with the addition of cyclohexane yielding a feed composition comprising 93 wt % cyclohexanone, 5 wt % cyclohexanol, and 2 wt % cyclohexane. FIG. 2 also shows that when the cyclohexene was replaced with 2 wt % cyclohexane, the catalyst activity remained the same for a further 600 hrs (i.e., from 1320 hours to 1920 hours time on stream) indicating that cyclohexane also improves the dehydrogenation catalyst stability. Under these conditions, the cyclohexane is converted to benzene via cyclohexene. At approximately 1400 hours of total time on stream, the unit was restarted after a nonproper shutdown. This startup and shutdown is shown FIG. 2 by a step change in conversion and selectivity. This decrease in conversion was due to the shutdown and startup and not the switch to cyclohexane.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for the dehydrogenation of at least one dehydrogenatable hydrocarbon, the process comprising:
   (a) supplying a dehydrogenation feed stream comprising at least one dehydrogenatable hydrocarbon to a first dehydrogenation reaction zone wherein the at least one dehydrogenatable hydrocarbon is an oxygen-containing six-membered carbon ring compound;
   (b) supplying at least one stabilizing compound to the first dehydrogenation reaction zone, such that the weight ratio of the stabilizing compound to the dehydrogenatable hydrocarbon supplied to the first dehydrogenation reaction zone is in the range of from 1:200 to 200:1 wherein the stabilizing compound is a non-oxygen-containing six membered carbon ring compound;
   (c) contacting the at least one dehydrogenatable hydrocarbon and the at least one stabilizing compound with a first dehydrogenation catalyst in the first dehydrogenation reaction zone under dehydrogenation conditions to convert at least a portion of the dehydrogenatable hydrocarbon into an unsaturated six-membered carbon ring compound and hydrogen;
   (d) contacting benzene and hydrogen with a hydroalkylation catalyst under hydroalkylation conditions to produce a hydroalkylation reaction product stream comprising cyclohexylbenzene, cyclohexane, and benzene;

(e) oxidizing at least a portion of the cyclohexylbenzene from the hydroalkylation reaction product stream to produce cyclohexylbenzene hydroperoxide;

(f) cleaving at least a portion of the cyclohexylbenzene hydroperoxide from the oxidizing step (e) to produce a cleavage reaction product stream comprising phenol and cyclohexanone;

(g) employing at least a portion of the cleavage reaction product stream as the dehydrogenation feed stream in step (a);

(h) dividing at least a portion of the hydroalkylation reaction product stream into (i) a $C_6$ stream comprising cyclohexane and benzene; and (ii) a cyclohexylbenzene stream; and (i) supplying at least a portion of the $C_6$ stream to the first dehydrogenation reaction zone as the at least one stabilizing compound.

2. The process of claim 1, wherein the weight ratio of the stabilizing compound to the dehydrogenatable hydrocarbon supplied to the first dehydrogenation reaction zone is in the range of from 1:100 to 10:1.

3. The process of claim 1, wherein the weight ratio of the stabilizing compound to the dehydrogenatable hydrocarbon supplied to the first dehydrogenation reaction zone in the range of from 1:200 to 1:1.

4. The process of claim 1, wherein the at least one stabilizing compound is selected from cyclohexane, benzene and mixture thereof.

5. The process of claim 1, wherein the at least on stabilizing compound is cyclohexane.

6. The process of claim 1, wherein the at least one stabilizing compound is benzene.

7. The process of claim 1, wherein the at least one dehydrogenatable hydrocarbon is cyclohexanone and the unsaturated six-membered carbon ring compound is phenol.

8. The process of claim 1, wherein at least a portion of the cyclohexane in the $C_6$ stream is converted to benzene by the contacting step (c) and at least a portion of the benzene is recycled to the contacting step (d).

9. The process of claim 1, and further comprising supplying a further portion of the $C_6$ stream to a second dehydrogenation reaction zone and contacting the further portion of the $C_6$ stream with a second dehydrogenation catalyst in the second dehydrogenation reaction zone under dehydrogenation conditions to convert at least a portion of the cyclohexane into benzene and produce a second dehydrogenation product stream.

10. The process of claim 1, and further comprising recycling at least a portion of the second dehydrogenation product stream back to the contacting step (d).

11. The process of claim 1, wherein at least a portion of the cleavage reaction product stream is supplied without fractionation to the first dehydrogenation reaction zone as the dehydrogenation feed stream.

12. The process of claim 1, and further comprising distilling at least a portion of the cleavage reaction product stream into (i) a first fraction comprising an azeotropic mixture of phenol and cyclohexanone; and (ii) a second cyclohexanone fraction.

13. The process of claim 12, wherein at least a portion of the first fraction is supplied to the first dehydrogenation reaction zone as the dehydrogenation feed stream.

14. The process of claim 12, wherein at least a portion of the second fraction is supplied to the first dehydrogenation reaction zone as the dehydrogenation feed stream.

15. The process of claim 1, wherein the hydroalkylation reaction product stream further comprises dicyclohexylbenzene and the dicyclohexylbenzene is converted to additional cyclohexylbenzene either by dealkylation or by transalkylation with benzene.

* * * * *